(12) United States Patent
Shkolnik

(10) Patent No.: US 7,160,266 B2
(45) Date of Patent: Jan. 9, 2007

(54) INFLATABLE BALLOON CATHETER WITH PURGE MECHANISM AND METHOD

(75) Inventor: Boris Shkolnik, Aventura, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 0 days.

(21) Appl. No.: 11/192,167

(22) Filed: Jul. 28, 2005

(65) Prior Publication Data

US 2006/0004344 A1    Jan. 5, 2006

Related U.S. Application Data

(60) Continuation of application No. 10/414,352, filed on Apr. 15, 2003, now abandoned, which is a division of application No. 09/578,317, filed on May 25, 2000, which is a continuation-in-part of application No. 09/487,128, filed on Jan. 19, 2000.

(51) Int. Cl.
*A61M 29/00* (2006.01)

(52) U.S. Cl. .................... 604/99.01; 604/509

(58) Field of Classification Search ............ 604/96.01, 604/508, 101.01, 101.05, 509, 99.01, 102.01, 604/102.03, 103, 103.01, 103.02, 103.03; 606/194–196; 128/898
See application file for complete search history.

(56) References Cited

U.S. PATENT DOCUMENTS

| 3,866,599 | A | 2/1975 | Johnson |
|---|---|---|---|
| 4,147,169 | A | 4/1979 | Taylor |
| 4,406,653 | A | 9/1983 | Nunez |
| 4,413,989 | A | 11/1983 | Schjeldahl et al. |
| 4,702,252 | A | 10/1987 | Brooks et al. |
| 4,744,366 | A | 5/1988 | Jang |
| 4,811,737 | A | 3/1989 | Rydell |
| 4,819,751 | A | 4/1989 | Shimada et al. |
| 4,850,348 | A | 7/1989 | Pell et al. |
| 4,938,220 | A | 7/1990 | Mueller, Jr. |
| 4,943,278 | A | 7/1990 | Euteneuer et al. |
| 4,981,478 | A | 1/1991 | Evard et al. |
| 4,994,072 | A | 2/1991 | Bhate et al. |
| 5,035,705 | A | 7/1991 | Burns |
| 5,049,130 | A | 9/1991 | Powell |
| 5,135,486 | A | 8/1992 | Eberle et al. |
| 5,176,661 | A | 1/1993 | Evard et al. |
| 5,176,698 | A | 1/1993 | Burns et al. |
| 5,195,969 | A | 3/1993 | Wang et al. |
| 5,195,972 | A | 3/1993 | Inoue |
| 5,226,889 | A | 7/1993 | Sheiban |
| 5,256,145 | A | 10/1993 | Atkinson et al. |
| 5,267,959 | A | 12/1993 | Forman |
| 5,429,605 | A | 7/1995 | Richling et al. |
| 5,514,073 | A | 5/1996 | Miyata et al. |
| 5,534,007 | A | 7/1996 | Germain et al. |
| 5,637,365 | A | 6/1997 | Carlblom |

(Continued)

FOREIGN PATENT DOCUMENTS

EP    0 366 478    5/1990

(Continued)

*Primary Examiner*—Nicholas D. Lucchesi
*Assistant Examiner*—Matthew F. DeSanto
(74) *Attorney, Agent, or Firm*—Henry W. Collins

(57) ABSTRACT

An improved balloon catheter which includes a purge mechanism for purging air from the catheter prior to use. The purge mechanism is sized to allow air to pass through, but highly restricts the flow of liquids. Air remaining in the catheter after purging is allowed to diffuse through the balloon prior to use. The mechanism is especially useful with low-pressure, gas-permeable, compliant balloons.

2 Claims, 3 Drawing Sheets

U.S. PATENT DOCUMENTS

| | | |
|---|---|---|
| 5,643,209 A | 7/1997 | Fugoso et al. |
| 5,700,243 A | 12/1997 | Narciso, Jr. |
| 5,711,754 A | 1/1998 | Miyata et al. |
| 5,728,063 A | 3/1998 | Preissman et al. |
| 5,728,065 A | 3/1998 | Follmer et al. |
| 5,749,849 A | 5/1998 | Engelson |
| 5,759,173 A | 6/1998 | Preissman et al. |
| 5,850,348 A | 12/1998 | Berman |
| 5,876,376 A | 3/1999 | Schwab et al. |
| 6,068,634 A | 5/2000 | Lorentzen Cornelius et al. |
| 6,102,891 A | 8/2000 | Maria van Erp |
| 6,139,525 A | 10/2000 | Davis-Lemessy et al. |
| 6,231,588 B1 | 5/2001 | Zadno-Azizi |
| 6,254,570 B1 | 7/2001 | Rutner et al. |
| 6,270,504 B1 | 8/2001 | Cornelius et al. |
| 6,375,637 B1 | 4/2002 | Campbell et al. |
| 6,517,548 B1 | 2/2003 | Lorentzen Cornelius et al. |

FOREIGN PATENT DOCUMENTS

| | | |
|---|---|---|
| NL | 1008178 | 2/1998 |
| WO | WO 00/64524 | 11/2000 |
| WO | WO 00/164524 | 11/2000 |
| WO | WO 80/01353 | 4/2003 |

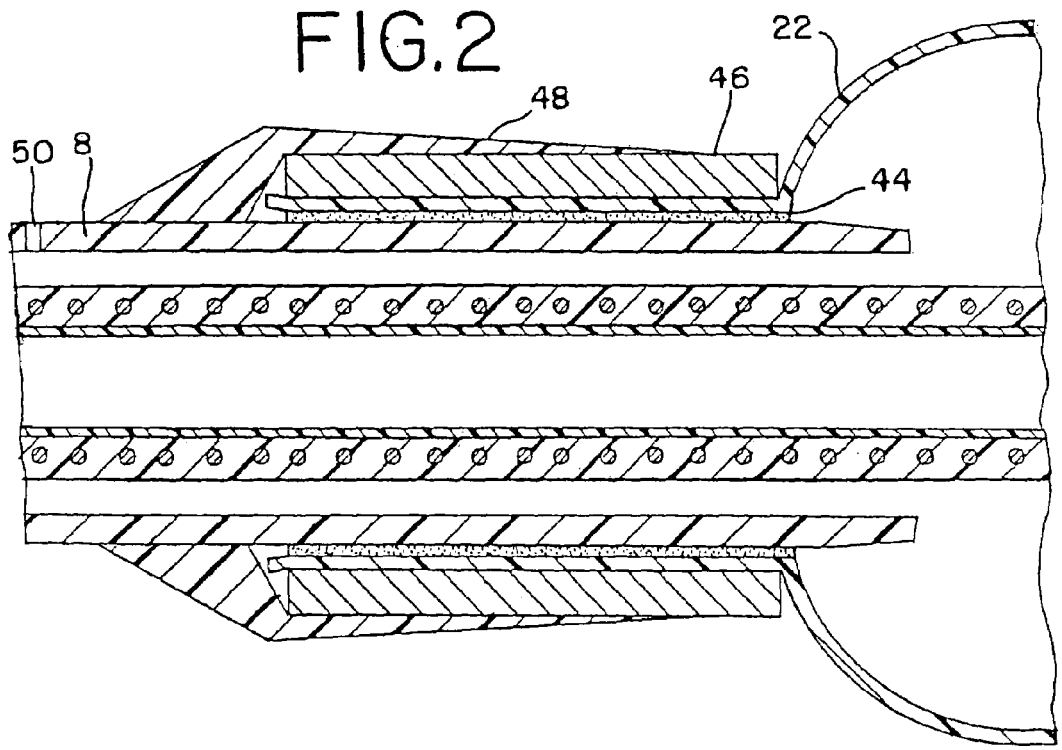
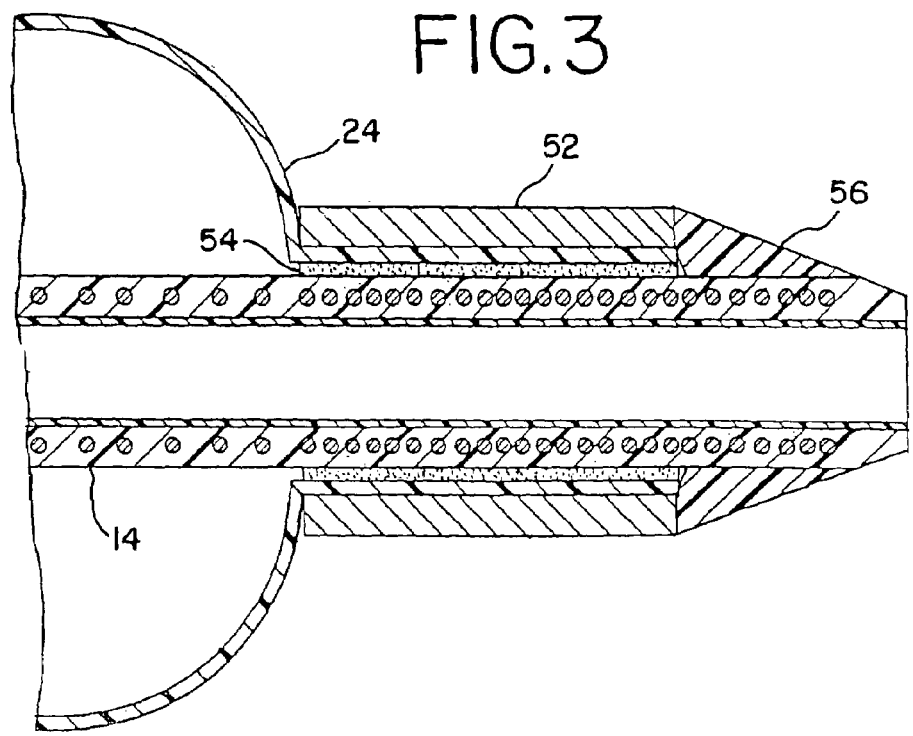

INFLATABLE BALLOON CATHETER WITH PURGE MECHANISM AND METHOD

CROSS-REFERENCE TO A RELATED APPLICATION

This application is a continuation of U.S. patent application Ser. No. 10/414,352, filed Apr. 15, 2003 now abandoned, which application was a division of U.S. patent application Ser. No. 09/578,317, filed May 25, 2000, which application was a continuation-in-part of U.S. patent application Ser. No. 9/487,128, filed Jan. 19, 2000, all of which are incorporated herein by reference.

BACKGROUND OF THE INVENTION

1. Field of the Invention

This invention relates to vascular balloon catheters which may be used for percutaneous transluminal angioplasty procedures, or alternatively may be used to position and expand a reinforcing stent within a blood vessel. In particular, this invention is especially adapted to treatment of small diameter blood vessels within the brain and may, for example, be used to temporarily occlude a blood vessel to evaluate the results of the occlusion prior to placing a permanent occlusion device within the vessel.

2. Description of the Prior Art

Medical catheters exist for a wide variety of purposes, including diagnostic procedures and interventional therapy, such as drug delivery, drainage, and perfusion. Catheters for each of these purposes may be introduced to numerous target sites within a patient's body by guiding the catheter through the vascular system. A wide variety of specific catheter designs have been proposed for such different uses.

Of particular interest to the present invention, small diameter tubular access catheters are presently being used for diagnostic and interventional therapy techniques for vessels within the brain, such as the imaging and treatment of aneurysms, tumors, arteriovenous malformations, and fistulas. Such techniques place a number of requirements on the catheters that are to be employed. The primary requirement is size. The blood vessels in the brain are frequently as small as several millimeters, or less, requiring that catheters have an outside diameter as small as one French (0.33 millimeters). In addition to small size, the brain vasculature is highly tortuous, requiring that catheters used in vessels of the brain be very flexible, particularly at their distal ends, to pass through the regions of tortuosity. Additionally, the blood vessels of the brain are relatively fragile, so it is desirable that the catheters have a soft, non-traumatic exterior to prevent injury.

In the case of balloon catheters, prior to introducing the catheter into a human body, it is desirable to purge air from the catheter with a liquid to prevent the air from being introduced into blood vessels. In the past, purging the catheter involved inflating the balloon section of the catheter to allow the air to escape out of the distal end of the balloon and then providing some mechanism to prevent air from reentering the balloon while it is being deflated.

U.S. Pat. No. 5,728,065 to Follmer, et al., discloses a balloon catheter with a vent hole disposed near the distal end of the balloon. The vent hole normally lays against the surface of an inner tubular member, preventing gases from entering the balloon. During purging, the balloon is inflated, the distal end of the balloon opens exposing the vent hole, and gases and a portion of the inflation medium flow out.

U.S. Pat. No. 4,811,737 to Rydell, discloses a balloon catheter with a slit in the distal portion of the tubular member. Fluid is injected into the catheter and flows through multiple inflation ports to expand the balloon. The purging fluid forces the air within the balloon through the slit in the tubular member.

SUMMARY OF THE INVENTION

In accordance with the present invention, there is a balloon catheter having a catheter body and an inflatable balloon. The catheter body comprises at least one tubular member having a tubular wall, a proximal end, a distal end, and having a lumen extending throughout the length of the tubular member. The inflatable balloon has a main body portion, a proximal portion, and a distal portion. The proximal portion and distal portion extend from the main body portion. The distal portion of the balloon is bonded to the tubular member near the distal end of the tubular member and the proximal portion of the balloon is bonded to the tubular member proximal to the distal portion of the balloon. The inflatable balloon is formed from a gas-permeable material. The balloon catheter also includes a coupling member mounted on the proximal end of the tubular member with the lumen of the coupling member in fluid communication with the lumen of the tubular member. A syringe or other hydraulic pressure device is coupled to the coupling member to apply a liquid within the lumen of the tubular member. In order to purge the system of air, at least one aperture extends radially through the wall of the tubular member at a point proximal to the proximal portion of the inflatable balloon.

In accordance with another aspect of the invention, there is a balloon catheter having a catheter body and an inflatable balloon. The catheter body includes an outer tubular member having a tubular wall, a proximal end, a distal end, and having a lumen extending throughout the length of the outer tubular member. The catheter body further includes an inner tubular member having a proximal end, a distal end, and a lumen extending therethrough. The inner tubular member is disposed coaxially through said lumen of the outer tubular member. The inflatable balloon has a main body portion and proximal and distal portions which extend from the main body portion. The proximal portion of the balloon is bonded to the distal end of the outer tubular member and the distal portion of the balloon is bonded to the distal end of the inner tubular member. The inflatable balloon is formed from a gas-permeable material. The balloon catheter also includes a coupling member mounted on the proximal end of the tubular member with the lumen of the coupling member in fluid communication with the lumen of the tubular member. A syringe or other hydraulic pressure device is coupled to the coupling member to apply a liquid within the lumen of the tubular member. In order to purge the system of air, at least one aperture extends radially through the wall of the tubular member at a point proximal to the proximal portion of the inflatable balloon.

In accordance with other aspects of the invention, the aperture is circular and has a diameter between approximately 0.0005 inches and 0.0014 inches, preferably about 0.0010 inches.

In accordance with another aspect of the invention, the liquid applied within the lumen of the tubular member exerts a fluid pressure between about 20 psi and 45 psi and thereby causes air to pass through the aperture.

In accordance with another aspect of the invention, the inflatable balloon is placed within a protective tube thereby restricting the ability of the balloon to inflate.

In accordance with another aspect of the invention, there is a method of purging air from a balloon catheter which includes the steps of: First, placing the inflatable balloon within a protective tube to restrict the inflation of the balloon. Second, injecting liquid into the lumen of the tubular member thereby forcing air to be evacuated from the balloon catheter through the purge aperture. Third, removing the protective tube. Fourth, inflating the balloon. Fifth, allowing any air remaining within the balloon to diffuse through the inflated balloon. And, finally, submerging the balloon in liquid while deflating the balloon to prevent air from re-entering the catheter body.

BRIEF DESCRIPTION OF THE DRAWINGS

FIG. 2 is a sectioned view of the catheter body near the proximal portion of the balloon;

FIG. 3 is a sectioned view of the catheter body near the distal portion of the balloon;

FIGS. 4 through 7 illustrate a sequence for purging the catheter wherein:

FIG. 4 shows the distal end of the catheter inside the protective tube;

FIG. 5 shows the balloon inflated within the protective tube;

FIG. 6 shows the balloon mostly deflated with the protective tube removed; and,

FIG. 7 shows the balloon normally inflated.

DESCRIPTION OF A PREFERRED EMBODIMENT

Figure 1:
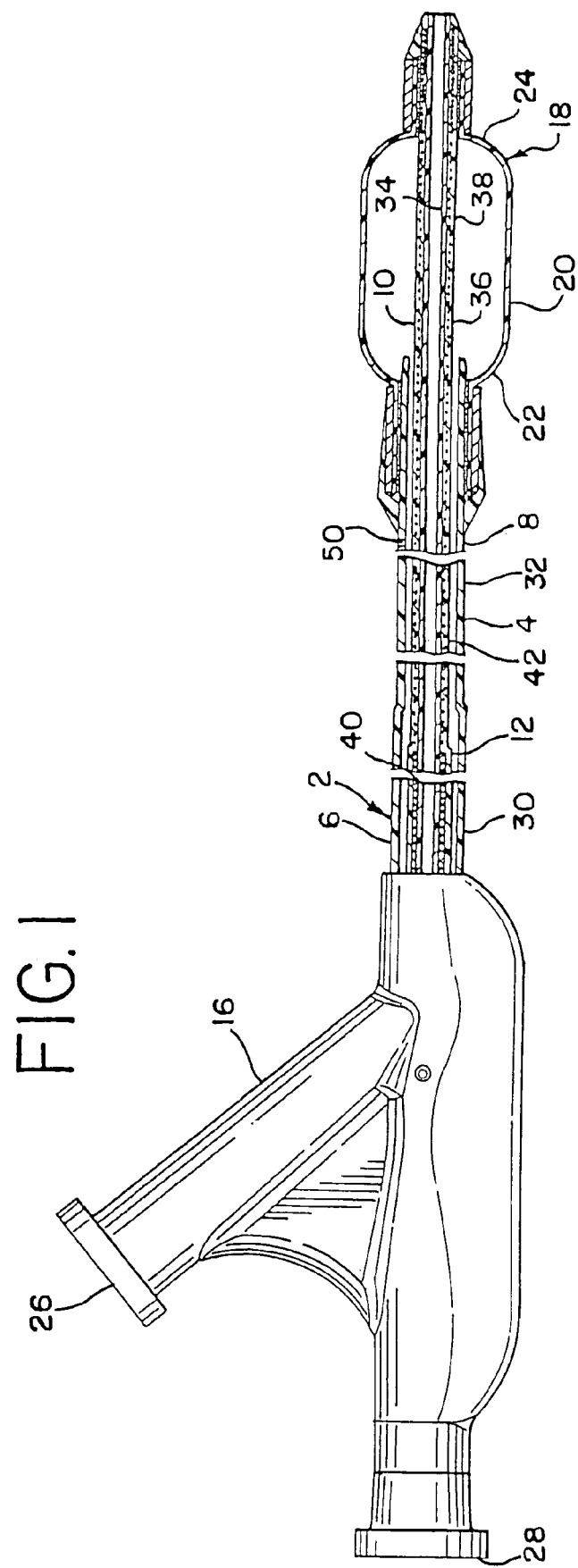
FIG. 1 is a partially sectioned view illustrating a balloon catheter made in accordance with the invention.

FIG. 1 illustrates a partial section view of a balloon catheter made in accordance with the present invention. The balloon catheter 2 includes an outer tubular member 4, having a proximal end 6 and a distal end 8, and an inner tubular member 10, having a proximal end 12 and a distal end 14. A dual port Y-connector 16 is coupled to the proximal end 6 of the outer tubular member 4 and the proximal end 12 of the inner tubular member 10. An inflatable balloon 18, having a main body portion 20, a proximal portion 22, and a distal portion 24, is secured to the distal end 8 of the outer tubular member 4 at the proximal portion 22 of the inflatable balloon 18. The distal portion 24 of the inflatable balloon 18 is, in turn, secured to the distal end 14 of the inner tubular member 10. With the balloon catheter of the present invention, fluid may be applied through a lumen in a side port 26 of the Y-connector 16 which communicates with the passageway between the inner tubular member 10 and the outer tubular member 4 to thereby inflate the balloon 18. Preferably, the fluid is applied using a syringe (not shown) coupled to the side port 26 of the Y-connector 16, although other means known to the art may be employed as well. In order to steer the catheter through the vasculature, a guidewire is typically passed through a proximal port 28 of the Y-connector 16 and through the lumen of the inner tubular member 10 which serves to assist in steering the distal tip of the catheter through the vasculature.

As illustrated, the outer tubular member 4 includes a proximal portion 30 and a distal portion 32 of differing diameters, with the proximal portion being larger than the distal portion. In addition, the proximal portion 30 is formed from nylon having a durometer of 75D and the distal portion 32 is formed of polyurethane having a durometer of 65D. The reduced diameter of the distal portion 32 of the outer tubular member 4, together with the decrease in durometer, results in the distal section of the catheter being more flexible and therefore may be more easily passed through the tortuous vessels of the human body.

The inner tubular member 10 is comprised of a thin inner layer 34, a reinforcing layer 36 placed on top of the inner layer 34 and a soft outer layer 38 which surrounds and bounds the reinforcing layer 36 to the inner layer 34. The reinforcing layer 36 is comprised of a proximal reinforcing layer 40 which is formed from braided stainless steel wires and a distal reinforcing layer 42 which is formed from a single helically wound platinum wire. The soft outer layer 38 is heat bonded onto the reinforcing layer 36. Accordingly, with the proximal section of the catheter having the inner tubular member formed with a braided reinforcing layer, this section of the catheter becomes relatively stiff and has a relatively high column strength so that the catheter may be pushed into and through the vasculature of the human body. On the other hand, the distal section of the catheter is formed with the inner tubular member comprised of a single helically wound wire which, while being sufficiently stiff to resist kinking, is still very flexible and is capable of traversing tortuous vessels.

As may now be appreciated, with the balloon catheter as illustrated in FIG. 1, the proximal section of the catheter is formed with an outer tubular member portion of an increased diameter and an inner tubular member which is formed by bonding a reinforcing layer of woven stainless steel wires between two polymer layers thereby providing a proximal catheter section which exhibits the characteristic of having relatively high column strength. The distal section of the catheter is formed with an outer tubular member having a reduced outer and inner diameter and with a single helically wound wire bonded between two polymer tubular members to thereby provide a distal section which is relatively kink resistant, but still remains very flexible.

FIG. 2 more clearly shows the balloon catheter near the proximal portion of the inflatable balloon. A first layer of adhesive material 44 is applied to a portion of the distal end 8 of the outer tubular member 4 and the proximal portion 22 of the balloon 18 is fit over the adhesive-covered portion. A first retaining ring 46 is positioned over the proximal portion 22 of the balloon 18 and is crimped onto the proximal end of the balloon, preferably using a crimping fixture. The first retaining ring 46 acts to reinforce the adhesive bond between the outer tubular member 4 and the proximal portion 22 of the balloon 18. A proximal marker band sleeve 48 is positioned over at least a half of the proximal end of the first retaining ring 46 and heat fused in place. The proximal marker band sleeve 48 prevents longitudinal movement of the first retaining ring 46 during balloon inflation and helps to ensure that the retaining ring does not become separated from the balloon catheter in the event the balloon ruptures.

A purge aperture 50 extends through a wall of the outer tubular member 4 at a point proximal to the proximal marker band sleeve 48. The sequence for purging the balloon using the purge aperture 50 is depicted in FIGS. 4 through 7, which are discussed in detail below.

FIG. 3 more clearly shows the balloon catheter near the distal portion of the inflatable balloon. The distal portion 24 of the balloon 18 is attached to the inner tubular member 10 by similar components used to attach the proximal portion. The distal end 14 of the inner tubular member 10 is inserted inside the distal portion 24 of the balloon. A second retaining ring 52 is positioned over the distal portion 24 of the balloon 18 and the distal end 14 of the inner tubular member 10. A second layer of adhesive material 54 is applied onto the distal end 14 of the inner tubular member 10 and under the distal portion 24 of the balloon 18, such that the inner surface of the distal portion 24 of the balloon is in contact with the second layer of adhesive material 54. The second retaining ring 52 is crimped onto the distal end of the balloon 18, preferably using a crimping fixture, and excess balloon material is trimmed distal to the second retaining ring 52. The distal marker band sleeve 56 is inserted over the distal end 14 of the inner tubular member 10. The distal marker band sleeve 56 is heat fused to the inner tubular member 10 distal to the second retaining ring 52.

Figure 4:
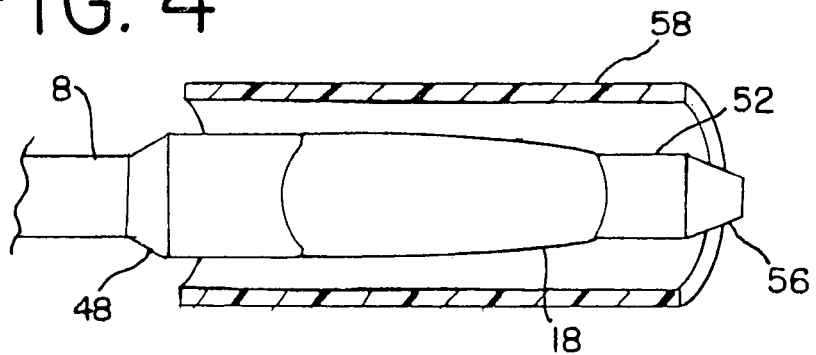

When purging the balloon catheter of air, the inflatable balloon 18 is placed within a protective tube 58, as shown in FIG. 4, to restrict the expansion of the balloon during purging. As can be appreciated, the protective tube 58 allows the balloon 18 to withstand the fluid pressure exerted during purging. Preferably, this pressure is between about 20 psi and 45 psi, but may be as high as 90 psi. Without the protective tube, the balloon would likely burst during inflation at these pressures. The protective tube 58 is preferably formed of a rigid polymer, but a metallic material could also be used. The inner diameter of the protective tube 58 should allow for some radial expansion of the inflatable balloon.

Figure 5:
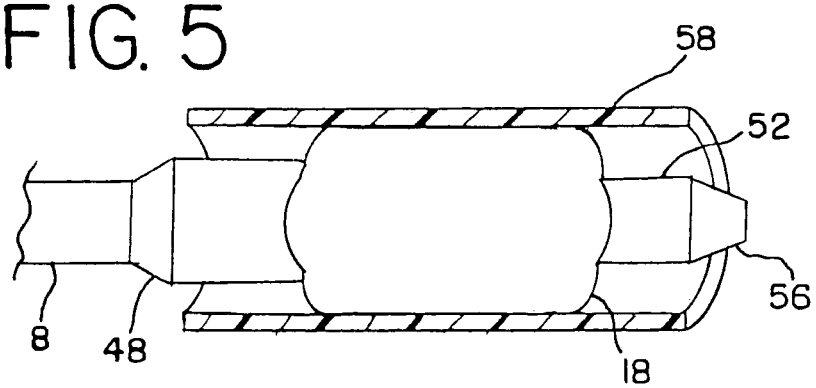
Figure 6:
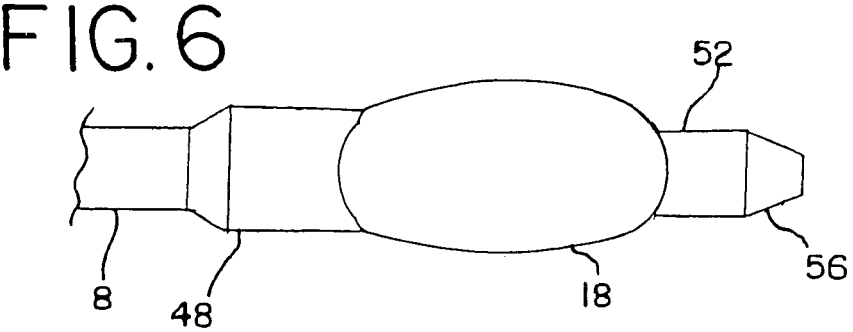

As shown in FIG. 5, the protective tube restricts the expansion of the balloon during purging and reduces the likelihood that the balloon will burst. Purging liquid is introduced through the lumen of the hub and into the inflation lumen of the catheter. As the liquid advances through the catheter body, air is forced through the purge aperture 50. Once the liquid reaches the purge aperture 50, the aperture is blocked and any air distal to the purge aperture is trapped within the inflatable balloon 18. Typically, a small drop of purge liquid forms at the location of the purge aperture to indicate that the catheter body has been purged of air. Once the catheter body has been purged, the protective tube 58 is removed, as shown in FIG. 6.

Figure 7:
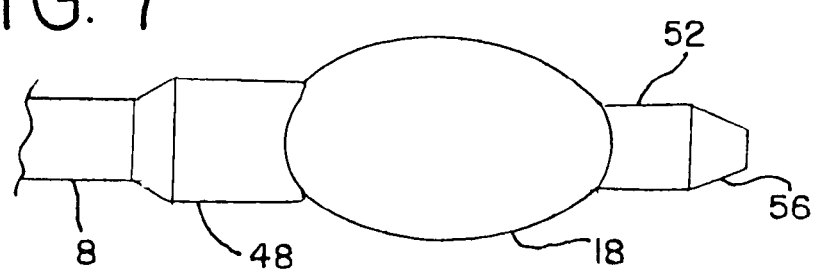

FIG. 7 shows the balloon after additional liquid has been introduced into the catheter body, thereby inflating the balloon. If air is observed within the balloon, the balloon is kept inflated to allow the air to diffuse through the wall of the inflated balloon. This extended inflation period also allows the user to visually inspect the balloon to ensure that the balloon was not damaged by the higher liquid pressure exerted during purging. Once all of the air has been removed from the balloon, the balloon is submerged in liquid to prevent air from re-entering the catheter while the balloon is deflated.

The first and second retaining rings, 46 and 52, respectively, are made of a radiopaque and biocompatible material, preferably gold, allowing for the precise positioning of the inflatable balloon as it is deployed into the human body. The marker band sleeves provide support for the retaining rings and prevent them from moving along the length of the outer or inner tubular members, especially when the balloon is inflated. Additionally, the marker band sleeves help to ensure that the retaining rings do not become separated from the assembly in the event that the balloon ruptures.

In a preferred construction of the present invention, the outer tubular member 4 is formed from polyurethane material and the inflatable balloon 18 is formed from a polyethylene elastomer or, preferably, a silicone material. The outside diameter of the proximal section of the outer tubular member 4 has an outside diameter of 0.043 inches and an inside diameter of 0.038 inches. The distal section of the outer tubular member 4 has an outside diameter of 0.0365 inches and an inside diameter of 0.0315 inches. In addition, the thin inner layer 34 of the inner tube member 10 is formed from PTFE material and has a thickness of approximately 0.0015 inches. The soft outer layer 38 of the inner tubular member 10 is preferably formed of polyurethane material and has a thickness of approximately 0.0025 inches.

The helical wound coil in the distal reinforcing layer 42 is formed of platinum wire having a circular cross section and with a diameter of approximately 0.0015 inches, and the braiding in the proximal reinforcing layer 40 is formed of stainless steel wire of circular cross-section. The wire forming the stainless steel braid preferably has a diameter of about 0.0015 inches.

The layers of adhesive material are formed from silicone approximately 0.001 inches thick. The length of the first layer is 0.040 inches and the length of the second layer is 0.023 inches. The first retaining ring 46 has a nominal diameter of 0.0375 inches and decreases by approximately 0.002 inches after being crimped. The first retaining ring 46 is approximately 0.040 inches wide. The second retaining ring 52 has a nominal diameter of 0.030 inches and decreases by approximately 0.0025 inches after being crimped. The second retaining ring 52 is approximately 0.023 inches wide.

The proximal marker band sleeve 48 is made from nylon material with an outer diameter of 0.0385 inches, an inner diameter of 0.036 inches, and a length of 0.040 inches. The proximal marker band sleeve 48 is positioned such that it overlaps at least half of the length of the first retaining ring 46. The distal marker band sleeve 56 is made from polyurethane material with an outer diameter of 0.0315 inches, an inner diameter of 0.0275 inches, and a length of 0.030 inches. The materials for the marker band sleeves were chosen relative to the durometers of the outer and inner tubular members that the marker band sleeves are attached to. The inner tubular member is more flexible than the outer tubular member is, so a more flexible material was chosen for the distal marker band sleeve.

The purge aperture 50 is preferably circular with a diameter between about 0.0005 and 0.0014 inches, with a diameter of about 0.0010 inches being preferred. The purge aperture is preferably formed using a heated wire, although other methods know to the art could be used as well. As can be appreciated, the purge aperture could take other shapes, such as an ellipse or rectangle. Multiple purge apertures of smaller dimension could also be employed.

The purge aperture 50 is located as close to the first retaining ring 46 as possible to allow as much air as possible to be purged from the catheter body. Typically, this distance is about 0.020 inches proximal to the first retaining ring. As can be appreciated, alternate methods of attaching the gas-permeable balloon to the catheter may be employed. In such cases, the purge aperture should be located as close to the proximal balloon-catheter junction as possible.

As can be appreciated, the purge mechanism of the present invention is applicable to other catheter configurations. For example, a single-lumen catheter could be used in place of the dual-lumen catheter described above. In such a case, the proximal and distal portions of the balloon would be attached to the same catheter body. Likewise, a multi-lumen configuration is also possible.

As is apparent, there are numerous modifications of the preferred embodiment described above that will be readily apparent to one skilled in the art to which this invention relates. These modifications are intended to be within the scope of the claims that follow.

That which is claimed is:

1. A method of purging air from a balloon catheter prior to insertion into a patient which includes a tubular member having a tubular wall and proximal and distal ends; an inflatable balloon having a main body portion and proximal and distal portions extending form said main body portion, said proximal and distal portions each being attached to the tubular member; a syringe coupled to the tubular member for applying a liquid within a lumen of the tubular member, a purge aperture extending through the wall of the tubular member at a point proximal to the proximal portion of the inflatable balloon; wherein the method includes the steps of:
    placing the inflatable balloon within a protective tube to restrict the inflation of the balloon;
    injecting liquid into the lumen of the tubular member thereby forcing air to be evacuated form the balloon catheter through the purge aperture;
    removing the protective tube;
    inflating the balloon following the removal of the protective tube;
    allowing any air remaining within the balloon to diffuse through the inflated balloon; and
    submerging the balloon in liquid while deflating the balloon to prevent air from re-entering the tubular member.

2. A method of purging air from a balloon catheter prior to insertion into a patient which includes a tubular member having a tubular wall and proximal and distal ends; an inflatable balloon having a main body portion and proximal and distal portions extending from said main body portion, said proximal and distal portions each being attached to the tubular member; a syringe coupled to the tubular member for applying a liquid within a lumen of the tubular member, a purge aperture extending through the wall of the tubular member at a point proximal to the proximal portion of the inflatable balloon; wherein the method includes the steps of:
    placing the inflatable balloon within a protective tube to restrict the inflation of the balloon;
    injecting liquid into the lumen of the tubular member thereby forcing air to be evacuated from the balloon catheter through the purge aperture;
    inflating the balloon following the removal of the protective tube; and
    allowing any air remaining within the balloon to diffuse through the inflated balloon.

* * * * *